(12) United States Patent
Dehdashtian

(10) Patent No.: US 6,702,255 B2
(45) Date of Patent: Mar. 9, 2004

(54) H-SHAPE DUCKBILL HEMOSTASIS VALVE ASSEMBLY INCLUDING GUIDE WIRE SEAL

(75) Inventor: Mark Dehdashtian, Costa Mesa, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 139 days.

(21) Appl. No.: 10/036,634

(22) Filed: Nov. 8, 2001

(65) Prior Publication Data

US 2003/0085373 A1 May 8, 2003

(51) Int. Cl.[7] .................. F16L 29/00; F16L 37/28; F16K 51/00
(52) U.S. Cl. ...................... 251/149.3; 137/846
(58) Field of Search .................. 251/149.3; 137/846

(56) References Cited

U.S. PATENT DOCUMENTS

| | | |
|---|---|---|
| 2,644,663 A | 7/1953 | Klingler |
| 3,422,844 A | 1/1969 | Grise |
| 4,341,239 A | 7/1982 | Atkinson |
| 4,436,519 A | 3/1984 | O'Neill |
| 4,524,805 A | 6/1985 | Hoffman |
| 4,535,819 A | 8/1985 | Atkinson et al. |
| 4,566,493 A | 1/1986 | Edwards et al. |
| 4,612,960 A | 9/1986 | Edwards et al. |
| 4,929,235 A | 5/1990 | Merry et al. |
| 5,010,925 A | 4/1991 | Atkinson et al. |
| 5,125,903 A | 6/1992 | McLaughlin et al. |
| 5,141,498 A | 8/1992 | Christian |
| 5,195,980 A | 3/1993 | Catlin |
| 5,301,707 A * | 4/1994 | Hofsteenge .................. 137/12 |
| 5,342,315 A | 8/1994 | Rowe et al. |
| 5,405,323 A | 4/1995 | Rogers et al. |
| 5,456,284 A | 10/1995 | Ryan et al. |
| 5,474,099 A * | 12/1995 | Boehmer et al. ........ 137/15.18 |
| 6,024,729 A | 2/2000 | Dehdashtian et al. |
| 6,305,420 B1 * | 10/2001 | Atkinson et al. ........... 137/846 |

FOREIGN PATENT DOCUMENTS

EP 993 839 A1 4/2000

* cited by examiner

Primary Examiner—Edward K. Look
Assistant Examiner—John K Fristoe, Jr.
(74) Attorney, Agent, or Firm—Lena I. Vinitskaya; Guy Cumberbatch

(57) ABSTRACT

A hemostasis valve for sealing around elongate medical instruments inserted into the body. The valve has an elastomeric valve body adapted to be received with a rigid introducer housing and seal thereagainst. The valve body has a distal end and a proximal end, and a cavity opening at the proximal end to receive the medical instruments. A pair of duckbill walls extends in the distal direction and converges and meets at a slit opening. The slit opening has an H-shape that effectively seals around multiple sizes of medical instruments, from the smallest catheter to the largest bore catheters. The duckbill walls may be planar or curvilinear, and may be reinforced with one or more ribs extending outward therefrom.

20 Claims, 4 Drawing Sheets

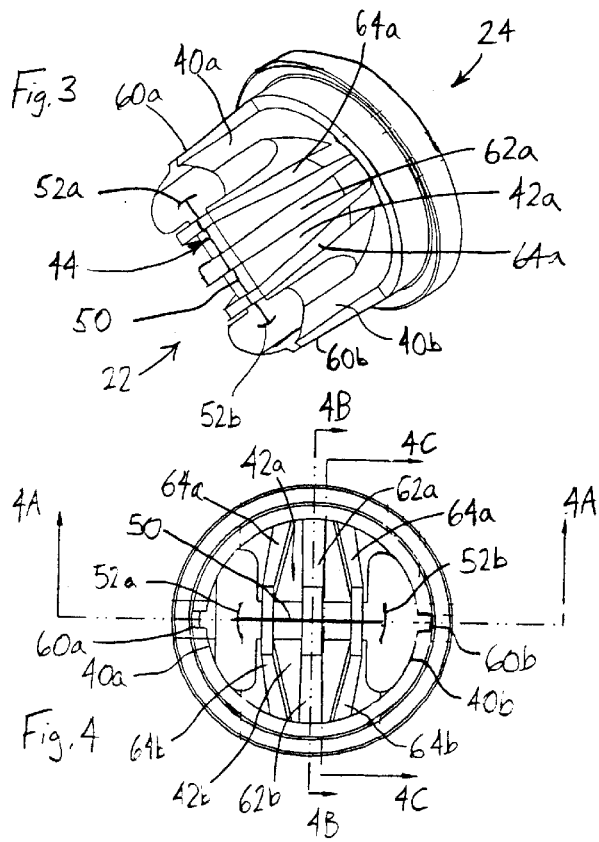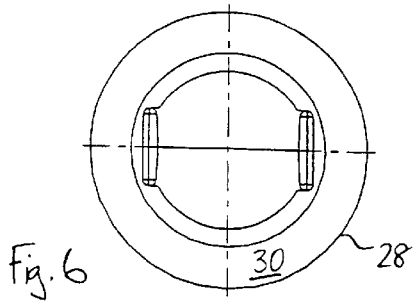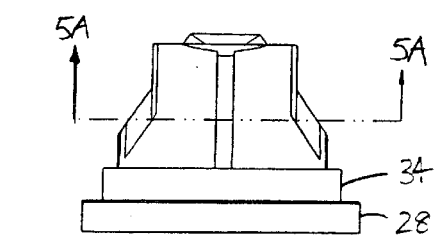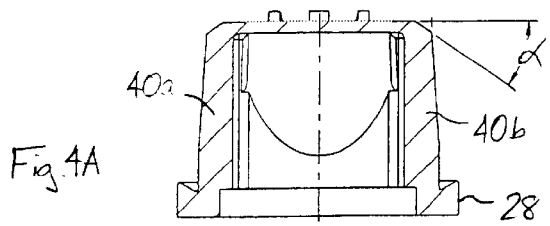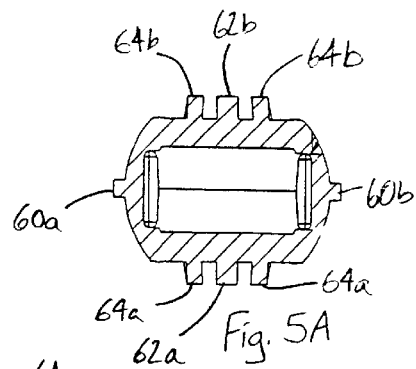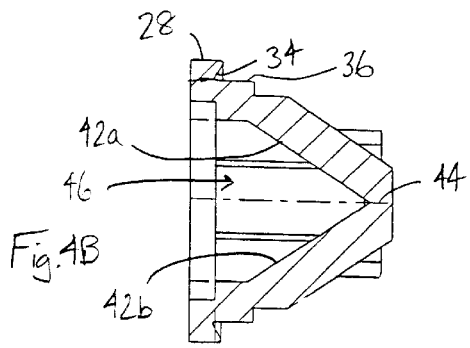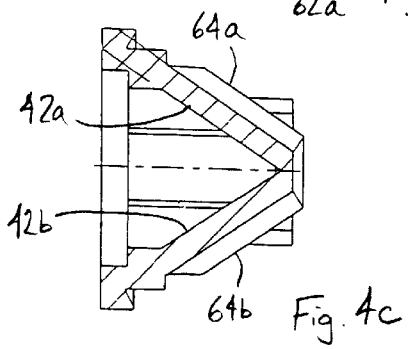

H-SHAPE DUCKBILL HEMOSTASIS VALVE ASSEMBLY INCLUDING GUIDE WIRE SEAL

FIELD OF THE INVENTION

The present invention relates generally to medical devices and, more particularly, to hemostasis valves for use within percutaneous catheter introducers.

BACKGROUND OF THE INVENTION

The use of catheter introducers in percutaneous medical procedures is well known in the art. A catheter introducer typically includes a long sheath having a first or proximal end positioned within a vein or artery of a patient and a second or distal end positioned immediately external to the epidermis of the patient. A lumen between the proximal and distal ends provides an access passageway for outside the body to the vein or artery lumen. Since the control of bleeding is obviously essential when such catheter introducers are utilized, conventional catheter introducers include a hemostasis valve assembly positioned at the proximal end of the sheath to permit a loader, catheter or other medical instrument to be introduced into the body of the patient through the sheath lumen while precluding blood from flowing out of the introducer.

In many percutaneous medical procedures, a small diameter guide wire is passed through the introducer sheath lumen and inserted into a vein or artery. The guide wire serves as a guide for a large diameter loader, catheter or other medical instrument employed later in the procedure. It is therefore necessary for the valve assembly to provide a sufficient seal around the small diameter guide wire to prevent excessive blood loss through the proximal end of the sheath. However, the valve assembly must also allow passage of, and sealingly engage, the large diameter loader, catheter, or other medical instrument, so as to prevent the flow of blood through the introducer.

One type of valve commonly used to control the flow of blood is referred to as a "duckbill" valve. A conventional duckbill valve includes a pair of walls, each having a generally planar configuration, which converge in the distal direction toward the patient and coapt or meet along a line or slit. In the absence of any instrument passed through the duckbill valve, the surrounding fluid exerts radial pressure on the convergent walls of the valve to help keep the slit closed. When an instrument such as a guidewire or catheter is inserted into a conventional duckbill valve, it passes between the converging walls of the valve and through the slit. This causes the walls to separate and to create an undesirable flow channel between the slit and the instrument, where the slit on either side of the instrument is slightly distended in a manner that resembles the corner of the eye. Therefore, duckbill valves are typically used in combination with another sealing member to prevent leakage.

U.S. Pat. No. 4,929,235 discloses a catheter introducer valve assembly designed to overcome the limitations of the prior art duckbill valves. The valve assembly includes a first valve having a Y-shaped slit which seals off any flow of blood from the sheath of the introducer during the time a catheter tube is not present. The first valve thus performs a function similar to that of a duckbill valve. A second valve, typically a disc seal with a small through-hole, seals around the catheter tube during and after the insertion of the catheter tube into the introducer so as to seal off any flow of blood.

Prior art catheter introducer valve assemblies have been successful in accomplishing the primary purpose of shutting off the flow of blood in the sheath when no medical instrument is present therein, and have been effective in allowing passage of and sealingly engaging the outer diameter of a catheter or other medical instrument, but have been unable to provide adequate seals around both a small diameter guide wire and a large diameter medical instrument passing through the introducer. The prior art valve assemblies typically include a seal which is adapted to sealingly engage around the relatively large diameter medical instrument such that no seal is formed around a relatively small diameter guide wire. With further reference to U.S. Pat. No. 4,929,235, the through-hole of the second valve has a diameter adapted to sealingly engage a catheter or loader having a diameter typically of approximately 0.3 inches. A typical guide wire has a diameter of approximately 0.035 inches such that once the catheter or loader has been removed, leaving the guide wire alone within the valve assembly, a substantial gap exists between the second valve and the guide wire whereby blood may pass through the introducer. Moreover, even the presence of a duckbill valve does not eliminate leakage around the guidewire because of the corner of the eye problem noted above.

Accordingly, there is a need for a catheter introducer valve assembly which provides for the effective sealing of blood flow during three separate and distinct conditions: when no medical instrument is inserted through the assembly, when a relatively large diameter medical instrument is inserted through the valve assembly, and when a relatively small diameter guide wire is inserted through the valve assembly. In addition, there is a need for a guide wire seal which provides an effective seal around the exterior of a guide wire which alone has been inserted through the valve assembly, but which also provides for the easy passage of a relatively large diameter catheter or loader.

SUMMARY OF THE INVENTION

The present invention provides a hemostasis valve assembly adapted for use within a catheter introducer. In a first mode of operation, the valve assembly seals blood from flowing through the catheter introducer when no instrument or device is passing therethrough. In a second mode of operation, the valve assembly seals around a relatively small diameter guide wire, while in a third mode of operation the valve assembly seals around a relatively large diameter elongated member or catheter. The valve assembly consistently and continuously seals off the flow of blood during all three modes of operation.

In accordance with one exemplary embodiment of the invention, a duckbill-type hemostasis valve for use in catheter introducer is provided. The valve has a valve body with a proximal end and a distal end, the valve body being sized to be received within a catheter introducer and being made of an elastomeric material. A slit opening in the valve body remains closed in the absence of a medical instrument passed through the introducer. The valve body includes an annular flange on the proximal end thereof defining on its exterior at least one sealing surface adapted to engage a complementary surface on the catheter introducer and prevent fluid flow therebetween. The annular flange circumscribes a proximal opening formed in the valve body and defines a central axis for the valve body. A pair of distally extending side walls connect to the annular flange and are opposed diametrically across the central axis. A pair of distally extending duckbill walls connect to the annular flange and are opposed diametrically across the central axis. The duckbill walls each extend between the two side walls and converge toward each other in the distal direction, wherein the distal end of the valve body is defined by the distal ends of the side walls and the duckbill walls.

The slit opening is formed in the distal end of the valve body and includes a middle segment that forms a separating line between the pair of duckbill walls. The slit opening further includes a pair of side segments disposed on either end of and generally perpendicular to the middle segment, the slit opening thus defining an H-shape and the distal ends of the side walls and the duckbill walls being joined together in a continuous manner surrounding the H-shaped slit opening.

Optionally, at least one reinforcing rib is provided on each duckbill wall that extends generally in a plane parallel to the central axis and biases the opposed duckbill walls toward each other. The reinforcing ribs provided on each duckbill wall may lie in a plane that includes the central axis. Desirably, there are multiple reinforcing ribs provided on each duckbill wall, and more preferably there are three reinforcing ribs provided on each duckbill wall, a middle one of which lies in a plane that includes the central axis. The middle reinforcing rib is thicker than the others.

The duckbill walls may be generally planar, or may be concavely curved with respect to the exterior of the valve body. The side walls are desirably curved generally about the central axis. Preferably, the middle segment of the slit opening is linear, while the side segments of the slit opening are curved and generally centered about the central axis.

In accordance with another embodiment of the invention, a duckbill-type hemostasis valve for use in catheter introducer comprises a valve body having a proximal end and a distal end, the valve body being sized to be received within a catheter introducer and being made of an elastomeric material. A slit opening remains closed in the absence of a medical instrument passed through the introducer. The valve body defines a central axis and, on its exterior, at least one sealing surface adapted to engage a complementary surface on the catheter introducer and prevent fluid flow therebetween. A pair of distally extending side walls are diametrically opposed across the central axis, and a pair of distally extending duckbill walls connected to the side walls are diametrically opposed across the central axis, the duckbill walls each extending between the two side walls and converging toward each other in the distal direction. The distal end of the valve body is defined by the distal ends of the side walls and the duckbill walls.

At least one reinforcing rib provided on each duckbill wall extends generally in a plane parallel to the central axis and biases the opposed duckbill walls toward each other. The slit opening is formed in the distal end of the valve body and includes a middle segment that forms a separating line between the pair of duckbill walls. The slit opening further includes a pair of side segments disposed on either end of and generally perpendicular to the middle segment, the slit opening thus defining an H-shape and the distal ends of the side walls and the duckbill walls being joined together in a continuous manner surrounding the H-shaped slit opening

BRIEF DESCRIPTION OF THE DRAWINGS

FIG. 3 is a further perspective view of the distal end of the valve of FIG. 1;

FIG. 4 is a distal end elevational view of the valve of FIG. 1;

FIG. 4A is a horizontal cross-sectional view of the valve of FIG. 4, taken along line 4A—4A;

FIG. 4B is a vertical cross-sectional view of the valve of FIG. 4 taken along line 4B—4B through a central reinforcing rib on each side wall;

FIG. 5 is a side elevational view of the duckbill valve of the valve of FIG. 4;

FIG. 5A is a vertical cross-sectional side view of the valve of FIG. 5 taken along line 5A—5A;

FIG. 6 is a proximal end elevational view of the valve of FIG. 1;

DETAILED DESCRIPTION OF THE PREFERRED EMBODIMENTS

The following detailed description, and the figures to which it refers, are provided for the purpose of describing example(s) and specific embodiment(s) of the invention only and are not intended to exhaustively describe all possible examples and embodiments of the invention. In the following various figures identical elements and features are given the same reference number, and similar or corresponding elements and features are or may be given the same reference numbers followed by an a, b, c, and so on as appropriate for purposes of describing the various embodiments of the present invention.

Figure 1:
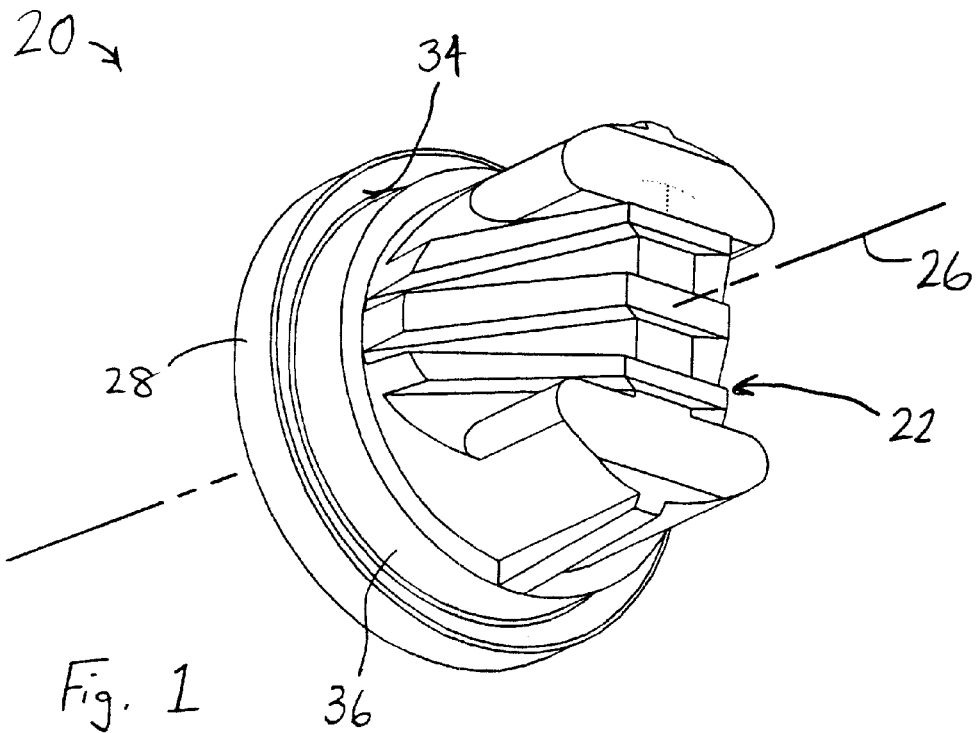
FIG. 1 is a perspective view of the outlet or distal end of an exemplary duckbill hemostasis valve of the present invention having three straight ribs reinforcing each side wall.
Figure 2:
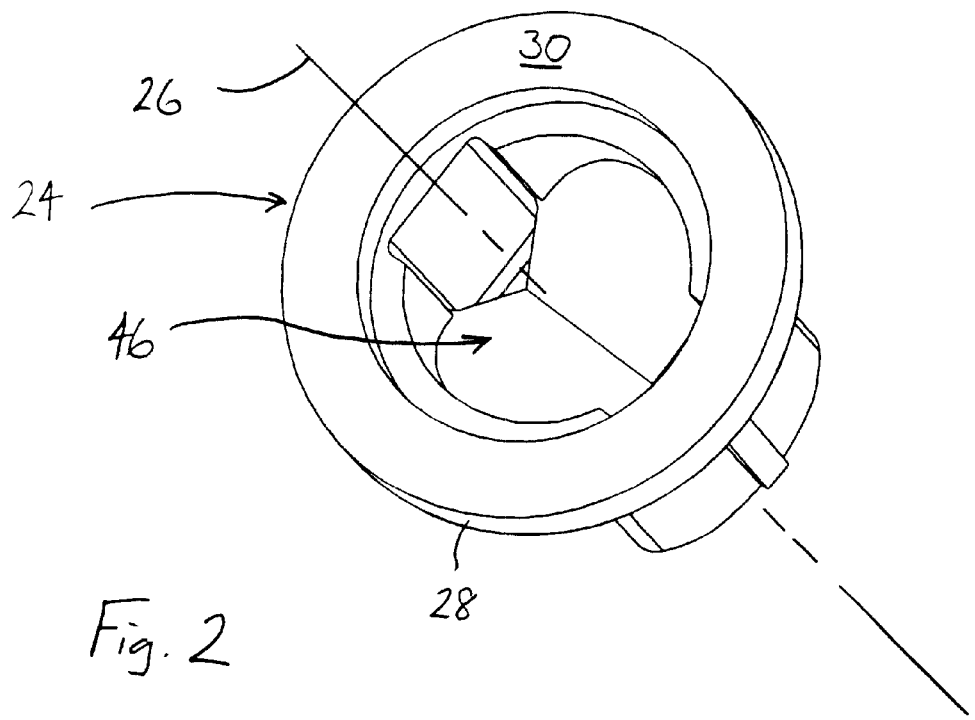
FIG. 2 is a perspective view of the inlet or proximal end of the valve of FIG. 1.

Referring initially to FIGS. 1 and 2, an exemplary medical hemostasis valve body 20 of the present invention has an outlet or distal end 22 opposite an inlet or proximal end 24 along a central axis 26. The terms inlet and outlet refer to the direction in which a medical instrument passes through the valve body 20. The valve body 20 includes a proximal annular flange 28 that forms a flat proximally-facing sealing surface 30 and extends outward from rest of the valve body 20 to define an annular groove 34 on its distal side. The valve body 20 is adapted to be received within a rigid catheter introducer, and thus the sealing surface 30 on the annular flange 28 engages a complementary surface on the catheter introducer and prevents fluid flow therebetween. Alternatively, the sealing surface 30 may form a fluid-tight seal against a medical connector used to couple to the introducer and securely deliver an instrument thereto.

With reference to FIGS. 1 and 4B, the proximal annular groove 34 adjoins an annular shoulder 36 that steps down in size to the distal instrument sealing portion of the valve body 20. The instrument sealing portion of the valve body 20 includes a pair of generally axially oriented side walls 40a, 40b that are diametrically opposed across the axis 26, as seen in cross-section in FIGS. 3 and 4A.

As seen in FIGS. 3, 4, 4B, and 5A, the side walls 40a, 40b are joined by a pair of duckbill walls 42a, 42b that converge in a distal direction from the annular shoulder 36 to meet at a sealing slit opening 44. The side walls 40a, 40b and duckbill walls 42a, 42b generally define a wedge-shaped hollow sealing portion that defines a cavity 46 therewithin (best seen in FIG. 2). The cavity 46 opens in a proximal direction at the proximal end 24 of the valve body 20 at the annular flange 28. Medical instruments may be passed into the cavity 46 from the proximal end and then through the slit opening 44. The valve body 20 is made of an elastomer, such as silicone, and the side walls 40a, 40b and duckbill walls 42a, 42b are relatively thin such that they deform outward at the slit opening 44 when a medical instrument is pushed therethrough.

As seen in FIGS. 3 and 4, the distal end 22 of the valve body 20 is formed by the combined distal ends of the side walls 40a, 40b and duckbill walls 42a, 42b. The slit opening 44 includes a middle segment 50 separating the pair of duckbill walls 42a, 42b, and a pair of side segments 52a, 52b disposed on either end of and generally perpendicular to the middle segment. The slit opening 44 thus resembles a short H-shape as seen in FIG. 4, or an I-shape if rotated 90°. The middle segment 50 is shown as linear, while the side segments 52a, 52b are curved about the axis 26, though the specific shape of these segments may vary. The side segments 52a, 52b distinguish the side walls 40a, 40b from the duckbill walls 42a, 42b, although these walls are continuous around the periphery of the distal end 22 of the valve body 20.

With reference to FIGS. 3–5A, the valve body 20 includes a plurality of reinforcing ribs that help maintain closure of the slit opening 44 with and without the presence of a medical instrument. Each side wall 40a, 40b has an axial rib 60a, 60b centered in the diametric plane in which the middle segment 50 of the slit opening 44 lies. The ribs 60a, 60b extend from the annular shoulder 36 to the distal end of the valve body 20, as best seen in FIG. 3. As seen in FIG. 4A, the distal end of each rib 60a, 60b is chamfered by an angle α of about 35° to facilitate insertion into a receiving catheter introducer. Each duckbill wall 42a, 42b has a middle rib 62a, 62b and a pair of secondary ribs 64a, 64b that are spaced from and on either side thereof. Each of the ribs 62a, 62b, 64a, 64b has a mirror image on the other duckbill wall 42a, 42b that meet at the distal end 22 and thus the valve body 20 appears to have three ribs altogether. The duckbill walls 42a, 42b and the adjoining ribs 60, 62, 64 are planar or linear.

FIG. 4 illustrates the respective widths and angular orientations of the ribs 62a, 62b, 64a, 64b. Namely, the middle ribs 62a, 62b are relatively thicker than the secondary ribs 64a, 64b and are aligned in a diametric plane perpendicular to the middle segment 50 of the slit opening 44. Each pair of secondary ribs 64a, 64b on each duckbill wall 42a, 42b, on the other hand, diverges in the distal direction. All six ribs 62a, 62b, 64a, 64b project distally beyond a flat face 66 defined in the distal end 22 as best seen in FIG. 4A.

As mentioned, the side walls 40a, 40b and duckbill walls 42a, 42b are relatively pliable and deform outward when a medical instrument such as a guidewire, a catheter, and endoscope, or the like passes through the valve body 20. The reinforcing ribs 60, 62, 64 buttress the walls without unduly sacrificing flexibility. In this way, the slit opening 44 is highly conformable around any instrument passed therethrough, and is more tightly sealed therearound because of the radially inward bias of the additional material of the reinforcing ribs 60, 62, 64.

Moreover, the H-shaped slit opening 44 performs its sealing function around a wide variety of sizes of medical instruments, from the smallest guidewires to large bore catheters. Indeed, the maximum size of instrument around which the valve body 20 seals is only limited by the inner diameter of the annular shoulder 36, which can be up to 30 Fr mm [Mark, should this be a French size, or at least give the equivalent catheter size?] The middle segment 50 of the H-shaped slit opening 44 forms the fluid-tight seal around any instrument having a diameter up to the length of the middle segment. Passage of larger instruments causes the duckbill walls 42a, 42b to separate at the side segments 52a, 52b and the inner face of the side walls 40a, 40b then contact and form a seal with the instrument. This graduated expansion of the slit opening 44 outperforms earlier designs in terms of effectively sealing around the entire range of instrument sizes contemplated.

FIGS. 7–9C illustrate a further embodiment of a duckbill valve body 70 of the present invention having curved reinforcing ribs. The valve body 70 is in many ways similar to the valve body 20 described above, and as such includes a distal end 72 opposite a proximal end 74 spaced along a central axis 76. The valve body 70 is made of an elastomer and a proximal flange 78 provides a resilient sealing surface that cooperates with a receiving introducer housing (or a separate connector) to prevent fluid flow therebetween and around the exterior of the valve body 70.

Figure 9:
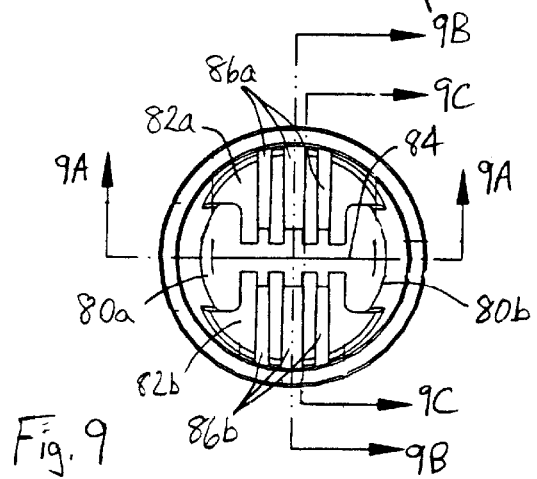
FIG. 9 is a distal end elevational view of the valve of FIG. 7.
Figure 9A:
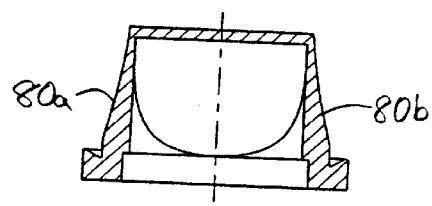
FIG. 9A is a horizontal cross-sectional view of the valve of FIG. 7, taken along line 9A—9A.
Figure 9B:
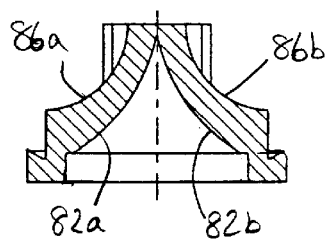
FIG. 9B is a vertical cross-sectional view of the valve of FIG. 7 taken along line 9B—9B through a central reinforcing rib on each side wall.

With specific reference to FIGS. 9–9B, the distal sealing portion of the valve body 70 includes a pair of side walls 80a, 80b and a pair of duckbill walls 82a, 82b that meet at the distal end 72. As before, an H-shaped slit opening 84 in the distal end 72 provides a versatile sealing septum around a variety of differently-sized medical implements that may be passed through the valve body 70. The side walls 80a, 80b are generally axially disposed and curved about the axis 76. The duckbill walls 82a, 82b, on the other hand are concavely curved with respect to the exterior of the valve body 70, in contrast to the planar walls 42a, 42b of the first embodiment. In addition, as seen in cross-section in FIG. 9C, the duckbill walls 82a, 82b are thicker at their proximal ends than at their distal ends and thus have substantial bias inward against each other, yet are highly conformable about instruments passed through the H-shaped slit opening 84.

Figure 7:
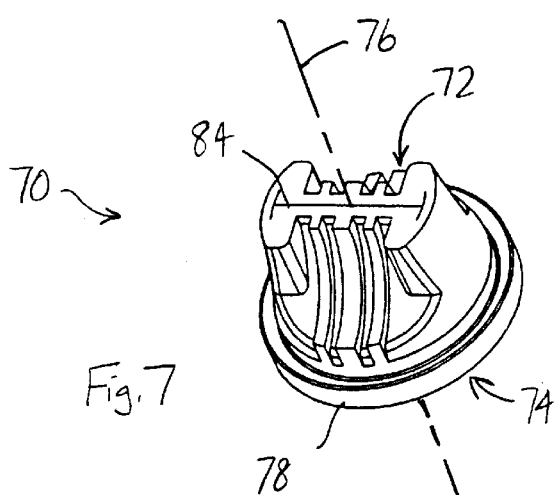
FIG. 7 is a perspective view of the outlet or distal end of an alternative duckbill hemostasis valve of the present invention having three curved ribs reinforcing each side wall.
Figure 8:
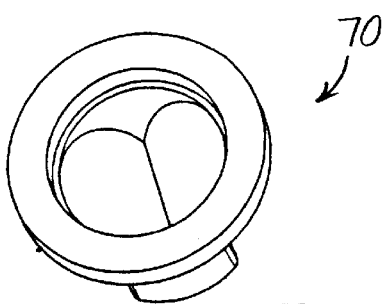
FIG. 8 is a perspective view of the inlet or proximal end of the valve of FIG. 7.
Figure 9C:
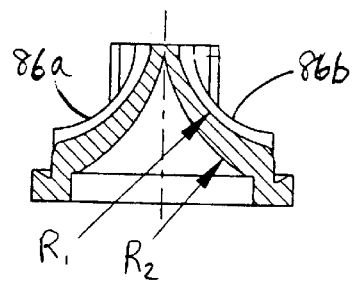
FIG. 9C is a vertical cross-sectional view of the valve of FIG. 7 taken along line 9C—9C in between two ribs.

As before, a plurality of reinforcing ribs help close the valve body around an instrument, or where no instrument is present. In this embodiment, there are no side ribs, but three ribs 86a, 86b on each of the duckbill walls 82a, 82b. As seen in FIG. 9, these ribs 86a, 86b are parallel to each other and the middle rib is thicker than the two flanking ribs. As seen in FIGS. 7 and 9B, the ribs 86a, 86b curve in the same direction as their respective host walls 82a, 82b. FIG. 9C shows that each of the duckbill walls 82a, 82b has an outer radius $R_1$ that is smaller than an inner radius $R_2$ such that each wall gradually thins from a proximal to a distal end. FIG. 9C also illustrates that the ribs 86a, 86b project outward from the respective host walls 82a, 82b by a uniform distance along their lengths.

Another exemplary hemostasis valve body 100 of the present invention can be seen in FIGS. 10–13. The valve body 100 exhibits a distal end 102 opposite a proximal end 104 along a central axis 106. Again, a proximal flange 108 provides a seal against the surrounding introducer housing and also potentially with the housing of a medical connector used to deliver a medical implement through the introducer.

Figure 10:
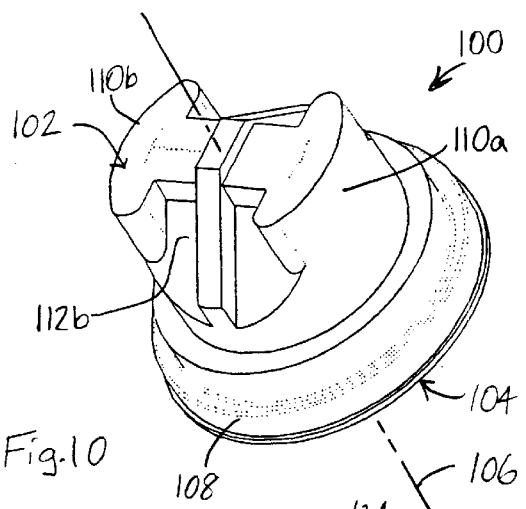
FIG. 10 is a perspective view of the outlet or distal end of another alternative duckbill hemostasis valve of the present invention having a single straight rib reinforcing each side wall.
Figure 11:
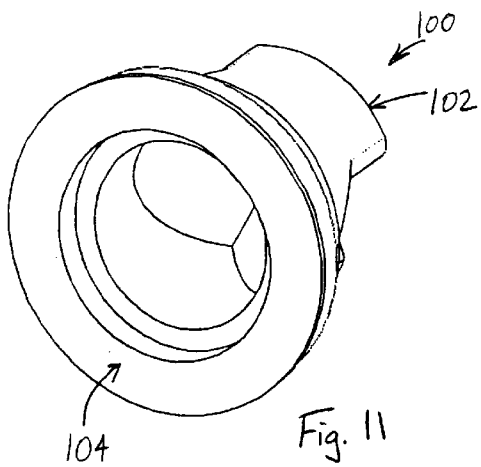
FIG. 11 is a perspective view of the inlet or proximal end of the valve of FIG. 10.
Figure 12:
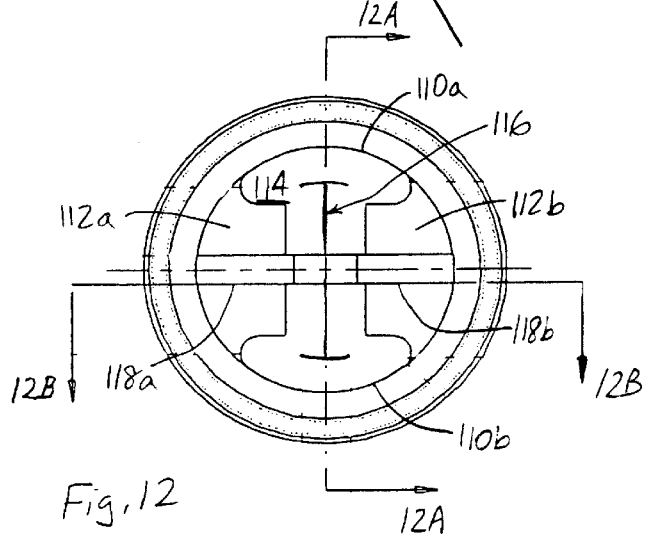
FIG. 12 is a distal end elevational view of the valve of FIG. 10.
Figure 13:
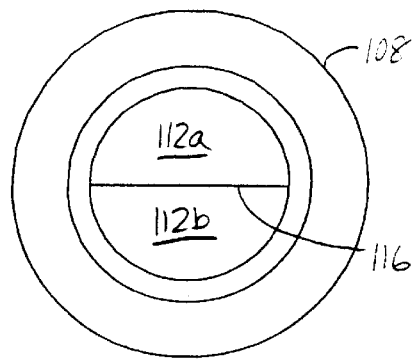
FIG. 13 is a proximal end elevational view of the valve of FIG. 10.
Figure 12A:
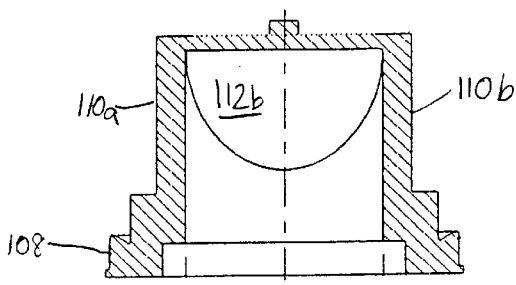
FIG. 12A is a horizontal cross-sectional view of the valve of FIG. 10, taken along line 12A—12A.
Figure 12B:
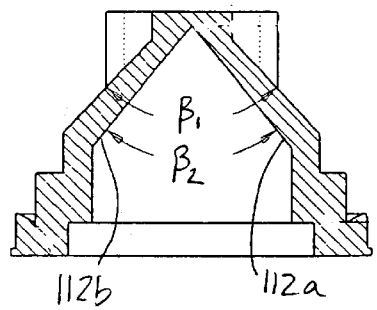
FIG. 12B is a vertical cross-sectional view of the valve of FIG. 10 taken along line 12B—12B through a central reinforcing rib on each side wall.

As seen in FIGS. 10 and 12–12B, the distal instrument sealing portion of the valve body 100 includes a pair of diametrically spaced axial side walls 110a, 110b and a pair of duckbill walls 112a, 112b therebetween. The side walls 110a, 110b are arcuate about the axis 106 and the walls 112a, 112b are planar as in the first embodiment. As seen in FIG. 12B, the walls 112a, 112b define an exterior included taper having an angle $\beta_1$ that is larger than the included internal taper angle $\beta_2$, such that the walls become thinner in the distal direction.

The walls 110, 112 terminate at a common distal face 114 that is flat and in a radial plane. An H-shaped septum or slit opening 116 is formed in the distal face 114 and performs a sealing function in the absence of and about any instruments passed through the valve body 100 from the proximal to the distal ends.

The valve body 100 has a single reinforcing rib 118a, 118b on each of the duckbill walls 112a, 112b that meet at the slit opening 116 and are perpendicular to a middle segment of the H-shaped opening. The ribs 118a, 118b project outward from both the respective duckbill walls 112a, 112b and the flat distal face 114. Again, the ribs 118a, 118b serve to close the valve body 100 yet do not unduly inhibit the highly flexible and conformable lips of the slit opening 116.

It will be appreciated that the invention has been described hereabove with reference to certain examples or preferred embodiments as shown in the drawings. Various additions, deletions, changes and alterations may be made to the above-described embodiments and examples without departing from the intended spirit and scope of this invention. Accordingly, it is intended that all such additions, deletions, changes and alterations be included within the scope of the following claims.

What is claimed is:

1. A duckbill-type hemostasis valve for use in catheter introducer, comprising:

a valve body having a proximal end and a distal end, the valve body being sized to be received within a catheter introducer and being made of an elastomeric material, and a slit opening that remains closed in the absence of a medical instrument passed through the introducer;

the valve body including an annular flange on the proximal end thereof defining on its exterior at least one sealing surface adapted to engage a complementary surface on the catheter introducer and prevent fluid flow therebetween, the annular flange circumscribing a proximal opening formed in the valve body and defining a central axis for the valve body;

the valve body including a pair of distally extending side walls connected to the annular flange and diametrically opposed across the central axis;

the valve body including a pair of distally extending duckbill walls connected to the annular flange and being diametrically opposed across the central axis, the duckbill walls each extending between the two side walls and converging toward each other in the distal direction, wherein the distal end of the valve body is defined by the distal ends of the side walls and the duckbill walls; and the slit opening being formed in the distal end of the valve body and including a middle segment that forms a separating line between the pair of duckbill walls, the slit opening further including a pair of side segments disposed on either end of and generally perpendicular to the middle segment, the slit opening thus defining an H-shape and the distal ends of the side walls and the duckbill walls being joined together in a continuous manner surrounding the H-shaped slit opening.

2. The duckbill valve of claim 1, further including at least one reinforcing rib provided on each duckbill wall that extends generally in a plane parallel to the central axis and biases the opposed duckbill walls toward each other.

3. The duckbill valve of claim 2, wherein the reinforcing ribs provided on each duckbill wall lie in a plane that includes the central axis.

4. The duckbill valve of claim 2, wherein there are multiple reinforcing ribs provided on each duckbill wall.

5. The duckbill valve of claim 4, wherein there are three reinforcing ribs provided on each duckbill wall, a middle one of which lies in a plane that includes the central axis.

6. The duckbill valve of claim 5, wherein the middle reinforcing rib is thicker than the others.

7. The duckbill valve of claim 1, wherein the duckbill walls are generally planar.

8. The duckbill valve of claim 1, wherein the duckbill walls are concavely curved with respect to the exterior of the valve body.

9. The duckbill valve of claim 1, wherein the middle segment of the slit opening is linear.

10. The duckbill valve of claim 9, wherein the side segments of the slit opening are curved and generally centered about the central axis.

11. A duckbill-type hemostasis valve for use in catheter introducer, comprising:

a valve body having a proximal end and a distal end, the valve body being sized to be received within a catheter introducer and being made of an elastomeric material, and a slit opening that remains closed in the absence of a medical instrument passed through the introducer;

the valve body defining on its exterior at least one sealing surface adapted to engage a complementary surface on the catheter introducer and prevent fluid flow therebetween, the valve body defining a central axis;

the valve body including a pair of distally extending side walls diametrically opposed across the central axis;

the valve body including a pair of distally extending duckbill walls connected to the side walls and being diametrically opposed across the central axis, the duckbill walls each extending between the two side walls and converging toward each other in the distal direction, wherein the distal end of the valve body is defined by the distal ends of the side walls and the duckbill walls;

at least one reinforcing rib provided on each duckbill wall that extends generally in a plane parallel to the central axis and biases the opposed duckbill walls toward each other; and the slit opening being formed in the distal end of the valve body and including a middle segment that forms a separating line between the pair of duckbill walls, the slit opening further including a pair of side segments disposed on either end of and generally perpendicular to the middle segment, the slit opening thus defining an H-shape and the distal ends of the side walls and the duckbill walls being joined together in a continuous manner surrounding the H-shaped slit opening.

12. The duckbill valve of claim 11, wherein the reinforcing ribs provided on each duckbill wall lie in a plane that includes the central axis.

13. The duckbill valve of claim 11, wherein there are multiple reinforcing ribs provided on each duckbill wall.

14. The duckbill valve of claim 13, wherein there are three reinforcing ribs provided on each duckbill wall, a middle one of which lies in a plane that includes the central axis.

15. The duckbill valve of claim 14, wherein the middle reinforcing rib is thicker than the others.

16. The duckbill valve of claim 11, wherein the duckbill walls are generally planar.

17. The duckbill valve of claim 11, wherein the duckbill walls are concavely curved with respect to the exterior of the valve body.

18. The duckbill valve of claim 11, wherein the side walls are curved generally about the central axis.

19. The duckbill valve of claim 11, wherein the middle segment of the slit opening is linear.

20. The duckbill valve of claim 18, wherein the side segments of the slit opening are curved and generally centered about the central axis.

* * * * *

UNITED STATES PATENT AND TRADEMARK OFFICE
CERTIFICATE OF CORRECTION

PATENT NO.    : 6,702,255 B2
DATED         : March 9, 2004
INVENTOR(S)   : Mark Dehdashtian It is certified that error appears in the above-identified patent and that said Letters Patent is hereby corrected as shown below:

<u>Column 6,</u>
Line 24, after "FR mm," delete "Mark, should this be a French size, or at least give the equivalent catheter size?"

Signed and Sealed this

Twenty-ninth Day of June, 2004

JON W. DUDAS
*Acting Director of the United States Patent and Trademark Office*